United States Patent [19]

Klein

[11] Patent Number: 5,449,621
[45] Date of Patent: Sep. 12, 1995

[54] METHOD FOR MEASURING SPECIFIC BINDING ASSAYS

[75] Inventor: Gerald L. Klein, Orange, Calif.

[73] Assignee: Biotope, Inc., Redmond, Wash.

[21] Appl. No.: 185,483

[22] Filed: Jan. 21, 1994

Related U.S. Application Data

[63] Continuation of Ser. No. 980,497, Nov. 23, 1992, abandoned, which is a continuation of Ser. No. 387,916, Jul. 31, 1989, abandoned.

[51] Int. Cl.$^6$ ...................... G01N 21/17; G01N 21/64
[52] U.S. Cl. ........................... 436/45; 436/164; 436/165; 436/172; 422/64; 422/67; 422/72; 422/82.05; 422/82.08; 422/82.09; 356/426
[58] Field of Search .................. 422/64, 67, 72, 82.05, 422/82.07, 82.08, 82.09; 436/164, 165, 172, 43, 45; 356/426, 427, 428

[56] References Cited

U.S. PATENT DOCUMENTS

| | | | |
|---|---|---|---|
| D. 273,807 | 5/1984 | Holen | D24/56 |
| D. 273,987 | 5/1984 | Holen et al. | D24/17 |
| D. 292,230 | 10/1987 | Holen | D24/22 |
| 4,135,883 | 1/1979 | McNeil et al. | 422/72 |
| 4,390,499 | 6/1983 | Curtis et al. | 422/64 |

(List continued on next page.)

FOREIGN PATENT DOCUMENTS

| | | | |
|---|---|---|---|
| 0160282 | 4/1985 | European Pat. Off. | B04B 5/04 |
| 0160901 | 4/1985 | European Pat. Off. | B04B 5/04 |
| 01160901 | 7/1989 | European Pat. Off. | B04B 5/02 |

OTHER PUBLICATIONS

Brochure, Olympus "Reply," Olympus Clinical Instruments Division, 4 Nevada Drive, Lake Success, N.Y. 11042-1179, (800) 223-0125, no publication date.
Newsletter with article on "Reply," Olympus Clinical Information Digest, vol. 2, No. 1, Early 1988.
Advertisement for Olympus "Reply", Olympus Corporation, Clinical Instruments Division, 4 Nevada Drive, Lake Success, N.Y. 11042-1179, no publication date.
Brochure, Kodak Ektachem Analyzers, Kodak Clinical Products, Eastman-Kodak Company, Jul. 1988.
Brochure, "The Vision system," Abbott Laboratories, North Chicago, Ill. 60064, (1-800-342-5228), Mar., 1985.
Brochure, Kodak Ektachem Analyzer Support & Service, Kodak Clinical Products, Rochester, N.Y. 14650, Sep. 1987.
Brochure, The Technicon RA-1000 system, Technicon Instruments Corporation, Feb. 1985.
Brochure, Technicon RA-1000 ISE Module, Technicon Instruments Corporation, 511 Benedict Avenue, Tarrytown, N.Y. 10591, Mar. 1984.
Brochure, Technicon Data Manager, Technicon Instruments Corporation, 511 Benedict Avenue, Tarrytown, N.Y. 10591-5097, 1984.

(List continued on next page.)

*Primary Examiner*—James C. Housel
*Assistant Examiner*—Jan M. Ludlow
*Attorney, Agent, or Firm*—Seed and Berry

[57] ABSTRACT

An automated patient sample analysis instrument uses assay cartridges which are pre-loaded with all reactants needed to perform an assay. Photometric measurements are performed on the cartridges while spinning at variable speeds in a centrifuge. Both axial and transverse measurements can be made on the cartridges. Multiple optical channels can be read by single detector. The instrument is well suited for low volume and for use by unskilled individuals. The photometric measurements are made by dividing the width of a measurement window into n intervals, measuring an optical result in one of the n intervals in each of n rotations of the cartridge, repeating the measurement process x times, summing or averaging the x results for each of the n intervals and selecting y of the largest resultant averaged or summed measurements as representative of the maximum measurement for the window.

7 Claims, 8 Drawing Sheets

U.S. PATENT DOCUMENTS

| | | | |
|---|---|---|---|
| 4,452,902 | 6/1984 | Suovaniemi et al. | 356/427 |
| 4,469,793 | 9/1984 | Guigan | 436/45 |
| 4,509,856 | 4/1985 | Lee | 356/246 |
| 4,549,809 | 10/1985 | MineKane et al. | 356/436 |
| 4,669,878 | 6/1987 | Meier | 436/164 |

OTHER PUBLICATIONS

Stratus Antiarrhythimc/Cardiac Glycoside Panel and Thyroid Panel, American Hospital Supply Corporation, P.O. Box 560672, Miami, Fla. 33152, 1987.

Article, "Two-Dimensional Centrifugation for Desk-Top Clinical Chemistry," *Clinical Chemistry*, vol. 31, No. 9, 1985.

Brochure, Reflotron, Boehringer Mannheim Diagnositcs, 9115 Hague Road, Indianapolis, Ind. 46250, 1985.

Brochure, Stratus Immunoassay System, American Hospital Supply Corporation, P.O. Box 560672, Miami, Fla. 33152. 1986.

Stratus "Farritin," American Hospital Supply Corporation, P.O. Box 560672, Miami, Fla. 33152, 1985.

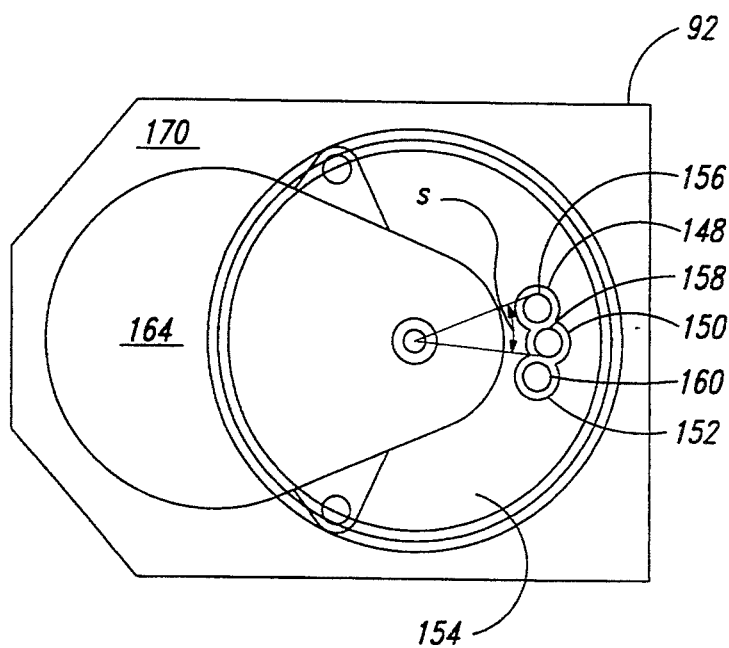
Fig. 5
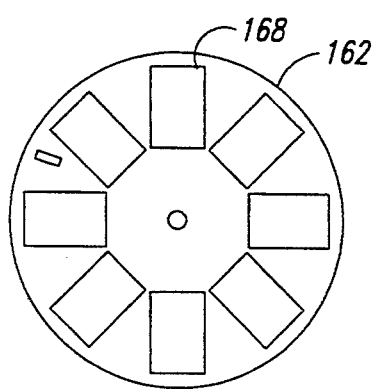
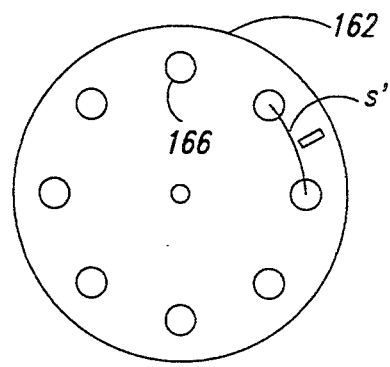
Fig. 6A   Fig. 6B

METHOD FOR MEASURING SPECIFIC BINDING ASSAYS

CROSS-REFERENCE TO RELATED APPLICATION

This application is a continuation of United States patent application Ser. No. 07/980,497, filed Nov. 23, 1992, now abandoned, which was a continuation of United States patent application Ser. No. 07/387,916, filed Jul. 31, 1989 now abandoned.

TECHNICAL FIELD

The invention generally relates to automated apparatus for performing quantitative assays of liquid samples. More specifically, the invention relates to methods and apparatus for performing photometric analysis of self-contained assay cartridges.

BACKGROUND OF THE INVENTION

Automated sample analysis devices have been developed to reduce human error in the performance of quantitative assays. Instruments of this type typically comprise apparatus used in industry and by laboratories to process hundreds or thousands of assays in a single day. These instruments are expensive and generally require the attention of a skilled technician for proper operation and to insure reliability of assay results.

A typical instrument used in high volume test environments is a large high throughput system offered by Olympus Clinical Instruments Division, under the trademark "REPLY." The "REPLY" instrument is a large system requiring approximately 7 feet by 11 feet of dedicated floor space and handles 400–600 tests per hour in a random access operating mode typical of moderate to high volume routine testing. The "REPLY" system requires 20 minutes warm-up time before being available to do testing. Additionally, trained technicians must install appropriate reagents, manage waste volumes and prime the system prior to initiating assays. In this and similar large test systems, proper use requires a high skill level and extensive training of operators to realize these benefits. Set up and calibration for all the reagents required to perform all anticipated assays from a large menu of test types (typically 70 different assays) must be accomplished prior to the system being available to perform all tests. This is inconvenient for less frequently ordered tests.

The operator of the above apparatus must prepare and replenish the reagents and monitor the apparatus' proper operation. In addition, the technician must be sufficiently competent to reconfigure the apparatus to perform different assays and various classes of assays.

In addition, although the apparatus described above is useful when conducting homogeneous assays, it is not well suited to conducting heterogeneous assays. Heterogeneous immunoassays, such as competitive assays, sandwich assays and sequential assays (such as those used for determination of the presence of hepatitis-B virus or the antigen to Human Immunodeficiency Virus), require long incubation times and separation of bound from free label, involving one or more washing steps which exceeds the capability of such apparatus.

For performing homogeneous assays, automated apparatus of the type described above have been very successful in large laboratories. However, such apparatus is not satisfactory for use in physicians' offices, by untrained personnel, or for processing a small number of samples. For this purpose, self-contained assay cartridges have been developed which contain all of the required reagents for performing an assay.

Such a cartridge for homogeneous assays is described in European Patent Application Publication No. 0,160,282 filed by Abbott Laboratories. An apparatus for processing the cartridge is described in European Patent Publication No. 0,160,901, also filed by Abbott Laboratories. The cartridge described in these applications is adapted to be received on a centrifuge which rotates about a rotation axis. The centrifuge is provided with axially displaced, secondary rotation axes to rotate the cartridge 90 degrees within the plane of the centrifuge. This compound, rotary motion is required to cause the reagents and patient sample to be appropriately metered and dispensed into various compartments. The cartridge is mechanically complex, relatively large and is expensive to manufacture.

In addition, because of the multi-dimensional type of motions required to process the contents of the cartridge, the apparatus described in EP 160,901 is also quite mechanically complex, and potentially unreliable. Further, this apparatus is not compact and is characterized by a significant noise level during operation.

Therefore, there is a need in the art for an automated apparatus capable of conducting both homogeneous and heterogeneous assays, which is compact, reliable and simple to operate. The apparatus should also be quiet during operation, and be capable of analyzing a variable number of processed or unprocessed samples for different tests without substantial modification of the instrument. The apparatus should be capable of using self-contained assay cartridges which can be automatically calibrated. The present invention fulfills this need and further provides other related advantages.

SUMMARY OF THE INVENTION

It is an object of the present invention to provide an automated analysis instrument for processing self-contained assay cartridges for both homogeneous and heterogeneous assays. The samples used within these assays may be processed or unprocessed samples (e.g., whole blood).

It is another object of the present invention to provide a method for determining an optical characteristic of an assay cartridge while rotating in a centrifuge at a range of speeds, including a high rate of speed.

It is another object of the present invention to provide a method for performing multiple optical measurements of a self-contained assay cartridge with a single detector.

It is yet another object of the present invention to achieve the above objects with an apparatus which can be operated by unskilled individuals.

The present invention achieves these objectives, and other objectives which will become apparent from the description which follows, by providing an automated analysis instrument having a variable speed centrifuge, at least one light emitting source positioned to direct a beam of interrogating light through self-contained assay cartridges at least one light detector and a mechanism for selectively transmitting light passing through the cartridge from the source to the detector. A controlling device is included to coordinate the actions of the instrument.

In a preferred embodiment, the instrument also includes an axial light emitting source positioned to direct a beam of interrogating light, filtered or unfiltered, axially towards one end of the tube for fluorescence and the like measurements when the cartridges are positioned in the centrifuge. A plurality of optical measurements are taken while the cartridges are spinning about a rotation axis for the centrifuge. Typically, the measurements are repeated while the centrifuge is spinning and, for a single determination, the repeated measurements are summed or averaged according to whether a fluorescence or an absorbance type measurement is being performed. The largest amplitude measurements of light intensity for each cartridge are then selected as indicative of the optical signal to be measured. This technique permits optical measurements of rapidly spinning cartridges to be taken with a high degree of accuracy.

Preferably, broad bandwidth light sources are used so that a variety of different assays using different wavelengths can be conducted. A device having a plurality of filters is provided to permit a selection of wavelengths for absorbance measurements to be made with the light sources.

The centrifuge can be contained in a temperature controlled cavity for incubating the cartridges. The rotation of the centrifuge can be controlled with a back-and-forth motion so that agitation is imparted to the cartridges during incubation.

A fast start-up time for the instrument is provided by compensating for variability of light source output with respect to time after optical measurements are taken.

The cartridges can be provided with a machine readable code, and the instrument can be provided with an optical scanning device for reading the codes to determine an instruction sequence which will be followed for the particular assay cartridge.

These and other objects of the present invention will become evident upon reference to the following detailed description and attached drawings.

BRIEF DESCRIPTION OF THE DRAWINGS

FIG. 5 is a top plan view of the mechanism shown in FIG. 3.

FIG. 6A is a front elevational view of a combination shutter/filter disk used in the channel and filter selection mechanism.

FIG. 6B is a rear elevational view of a combination shutter/filter disk illustrating the apertures which select one of three channels.

DETAILED DESCRIPTION OF THE INVENTION

Operation of the Instrument

Figure 1:
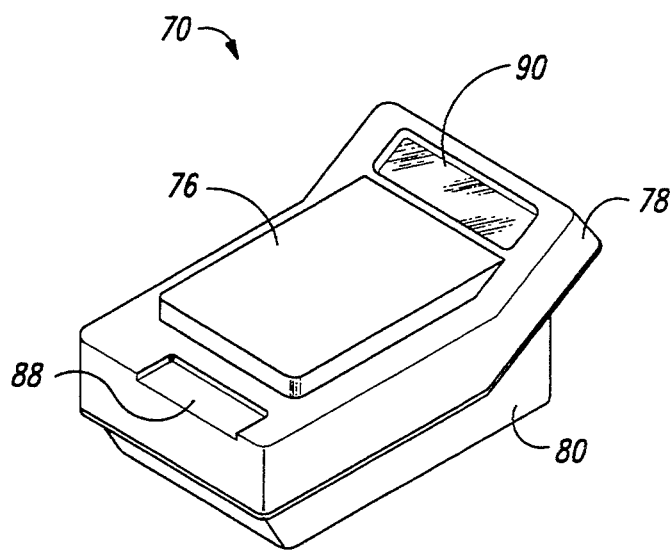
FIG. 1 is an isometric view of an automated patient sample analysis instrument in accordance with the present invention.

A representative automated sample analysis instrument, in accordance with the present invention, is generally indicated at reference numeral 70 in FIG. 1. The instrument is adapted to perform fully automated processing of a variety of assay cartridges, for instance of the type shown in FIGS. 10A and 10B. In general, suitable assay cartridges are self-contained and elongated, each cartridge defining a cartridge axis and having an optical measurement surface. Cartridges of the type shown in the figures are pre-loaded with one or more axially disposed immiscible layers. Other self-contained cartridges which do not have immiscible layers may also be used. Patient sample then is added to the cartridge and a releasable seal is broken to release reagent from a reservoir. Following a brief mixing cycle, patient sample then undergoes reaction with a variety of reagents. The cartridges are then centrifuged at high speeds for later photometric analysis. The instrument centrifuges, incubates, agitates and performs photometric analysis on the cartridges, and displays the results of each assay without operator assistance. The operator merely loads the cartridges with the patient sample (i.e., whole blood or serum), inserts the cartridges into the instrument and initiates the instrument. The instrument is well adapted for use in environments such as physicians' offices where a relatively low number of patient samples are to be tested in comparison to large commercial testing laboratories. This instrument is also well adapted for specialty tests in large laboratories. In addition, the instrument is particularly well suited for use by untrained personnel because all handling and loading of reagents, etc. is performed when the cartridges are manufactured. No fluid handling, preparation, cleaning or maintenance are needed.

Overview of the Instrument

Figure 10B:
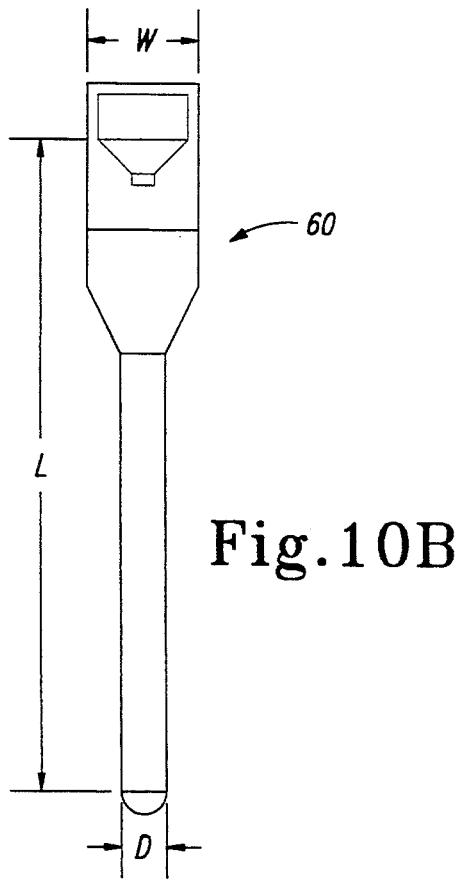
FIGS. 10A and 10B are schematic illustrations of self-contained assay cartridges for use with the automated analysis instrument of the present invention.
Figure 10A:
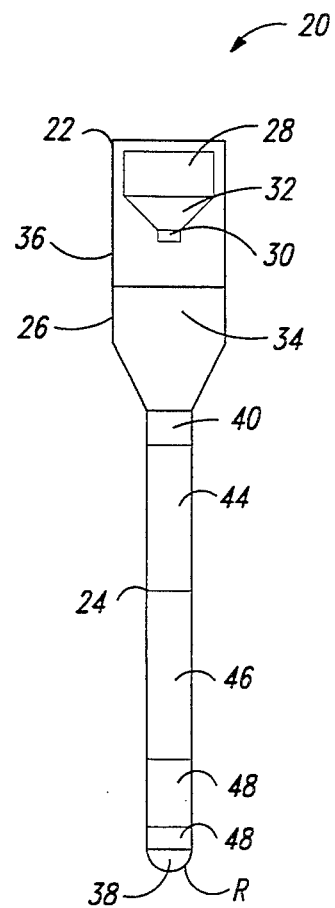

The representative instrument 70 has a rotatable cartridge carriage 72 adapted to receive a plurality of assay cartridges such as cartridges 20 and 60 in FIGS. 10A and 10B. The carriage is rotatably received in a bowl 74. The bowl may be manufactured from a material having low thermal conductivity and low thermal mass. The carriage is enclosed within the bowl by a pivotable lid 76 which entraps air within the bowl and provides light tightness and insulation to the area enclosed thereby.

The carriage 72, bowl 74 and pivotable lid 76 are contained in a housing shown in FIG. 1 having an upper portion 78 and a lower portion 80. The lower portion contains a power supply 82 and a printed circuit board containing a microprocessor 86 with associated memory and other electronic circuitry described hereinbelow for operating the instrument.

After loading patient samples into the cartridges 20, 60 and loading the cartridges into the carriage 72, the operator closes the lid 76 and initiates the instrument by pressing a start button 88. The instrument automatically performs all the necessary steps to complete the appropriate assay for the selected cartridge and displays the results on a display 90 for the operator. The results are also displayed by way of a printer 89 shown in FIG. 7. Minimal skills are required by the operator to perform any one of a variety of assays which have instructions stored in the associated memory of the microprocessor 86.

Assays which may be performed by the instrument 70 include assays for which an optical determination of the cartridge, such as absorbance, fluorescence, luminescence, light scattering, etc., is conducted. These photometric measurements are made by a detector assembly indicated by a bracket 92 in FIG. 2.

Figure 7:
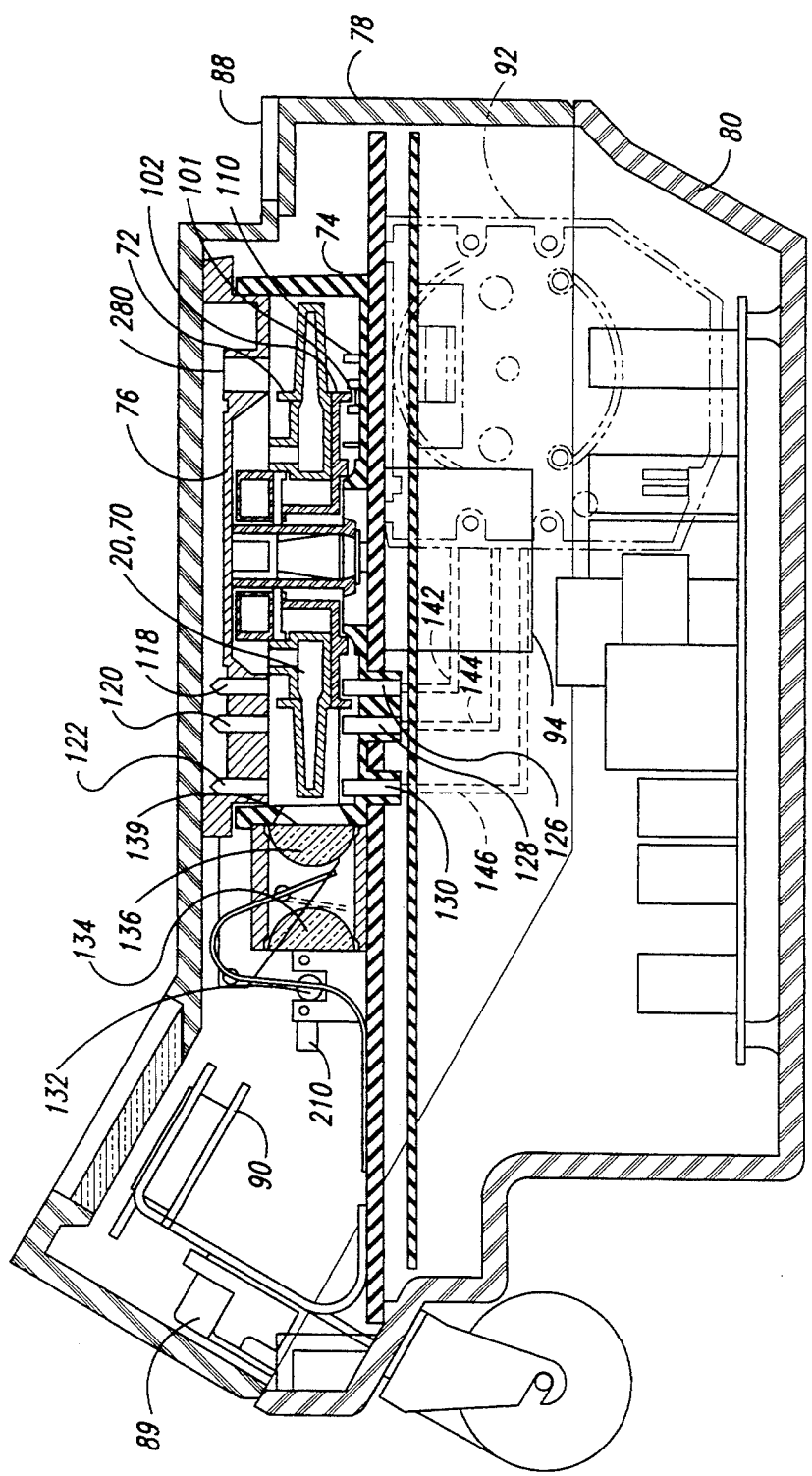
FIG. 7 is a sectional, side elevational view of the instrument shown in FIG. 1.
Figure 8:
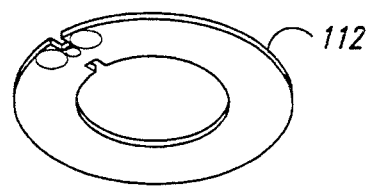
FIG. 8 is an exploded, isometric view of a bowl for partially enclosing a rotatable, cartridge carriage.
Figure 8:
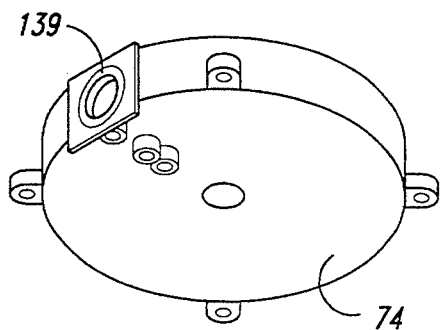
Figure 8:
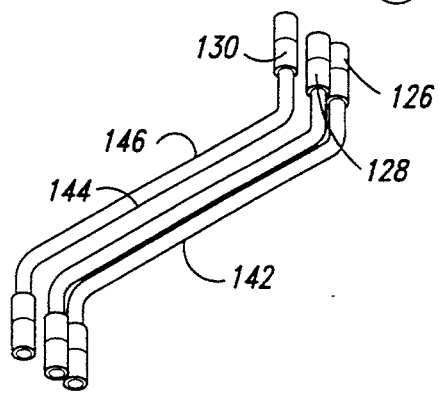
Figure 9:
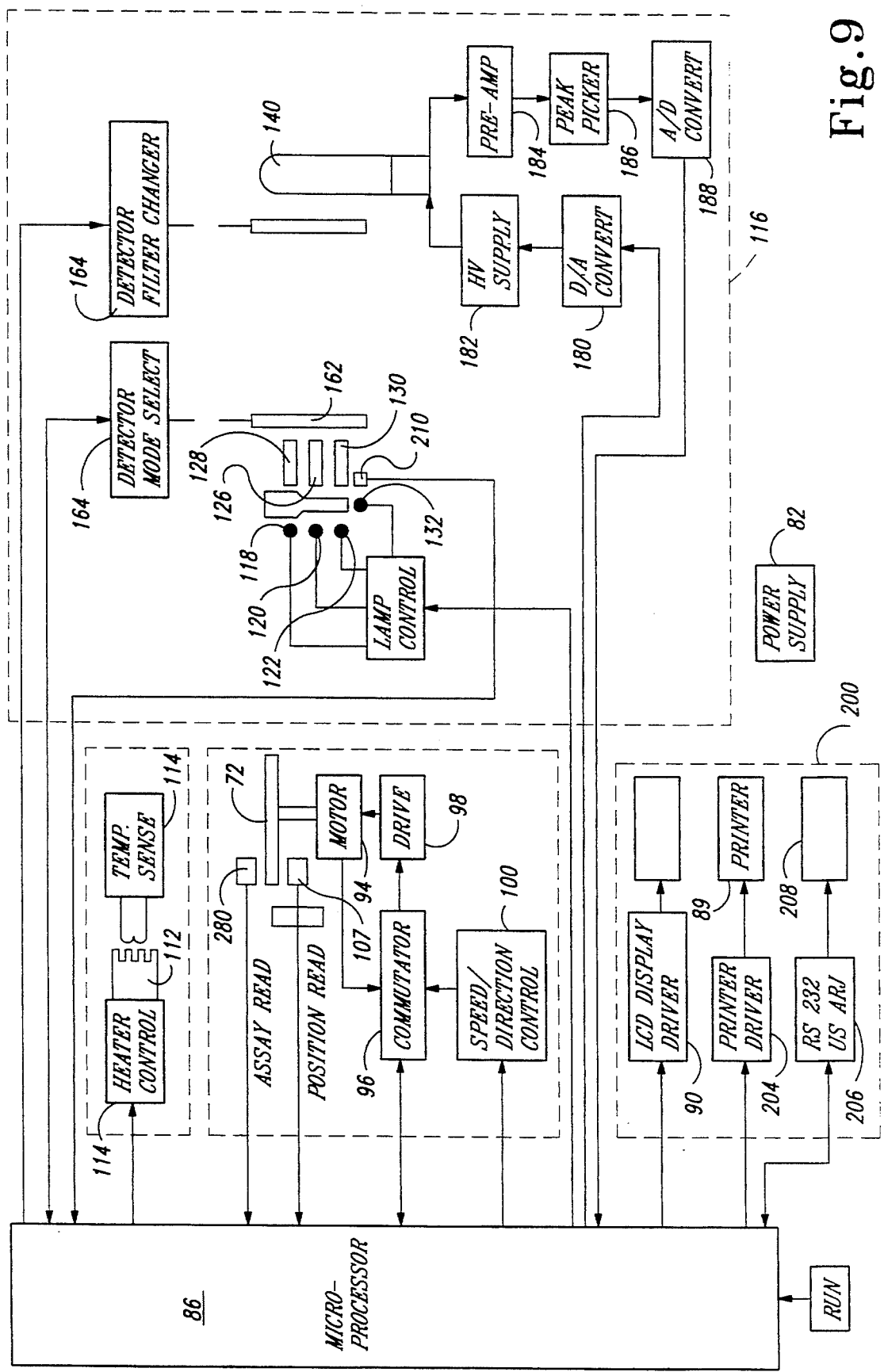
FIG. 9 is a schematic illustration of various operationally interrelated subassemblies of the instrument shown in FIG. 1.

FIG. 9 is a schematic representation of the cooperative relationship between various subassemblies of the instrument shown in FIGS. 1-8, 11 and 12. The microprocessor 86 controls the operation of the various subassemblies. A suitable microprocessor is a Zilog model Z-180 manufactured by Zilog, Inc., of Campbell, Calif. ROM (read only memory) devices (not shown) are also included on the printed circuit board 84 to provide the capacity for permanent memory containing a variety of programs for system control. Additional space for static random access memory devices is also provided.

The cartridge carriage 72 is driven by a motor, such as a 3-pole brushless direct current motor 94. The microprocessor 86 controls the motor through a conventional commutator 96 and drive circuit 98. A speed control circuit 100 utilizes pulse width modulation to control the speed of the motor under direction from the microprocessor 86. The speed of the carriage 72 is programmed to vary from a low speed to a high speed of up to 10,000 rpm for centrifuging and reading data. The carriage is also programmed to rotate at a very low speed to incubate and agitate cartridges received in the carriage. Agitation may be achieved by utilizing a convenient property of multi-pole DC motors. When agitating, the frequency of the pulse width modulated signal is set relatively low at approximately 3-30 Hz. The "on time" for a pulse is set short (0-10% of a full cycle). The motor is therefore energized during an "on time" so as to impart an acceleration towards the next adjacent pole. The motor is then de-energized well before it reaches the next pole while it is between poles. The rotor within the motor therefore accelerates in reverse back to the previous pole thereby imparting a mixing motion to the cartridge carriage 72. By varying the frequency of the drive signal and the "on time" of the pulses, the cartridge carriage 72 is made to precess (i.e., two steps forward, one step back) to slowly rotate the cartridges while agitating the cartridges.

The position and speed of the cartridge carriage 72 is monitored by an emitter/detector pair 101 positioned on opposite sides of a castellated ring 102, in this embodiment having twenty-four interruptions. A second castellated ring (not shown) having one interruption is monitored by a second emitter/detector pair 110 to serve as an index locater for the cartridge carriage 72.

As stated above and shown in the figures, the carriage 72 is rotatably received within a bowl 74. In order to maintain a temperature-controlled environment, the bowl contains an annular, resistive heater 112 (best seen in FIG. 8) connected to conventional heater control circuitry 114 under the control of the microprocessor 86. A conventional temperature sensor 114 (see FIG. 9) provides temperature information to the microprocessor 86 for controlling the heater 112. The rotation of the cartridge carriage 72 equalizes temperatures within the sealed bowl by stirring the air such that precise temperature control can be maintained merely by heating the air within the bowl. A fan may also be used to distribute the warm air.

Photometric System

Figure 3:
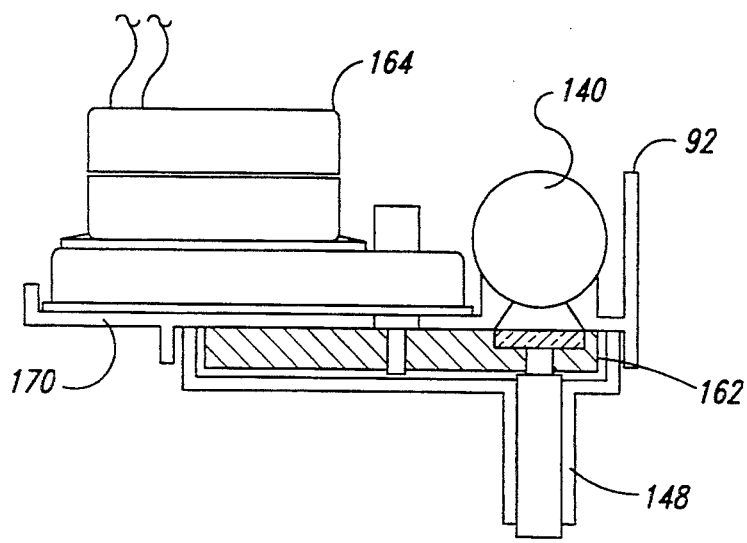
FIG. 3 is a side elevational view of a channel and filter selection mechanism of the instrument.
Figure 4:
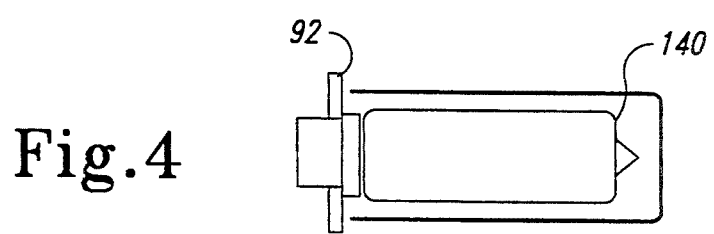
FIG. 4 is a side elevational view of the mechanism showing a photomultiplier tube.
Figure 11:
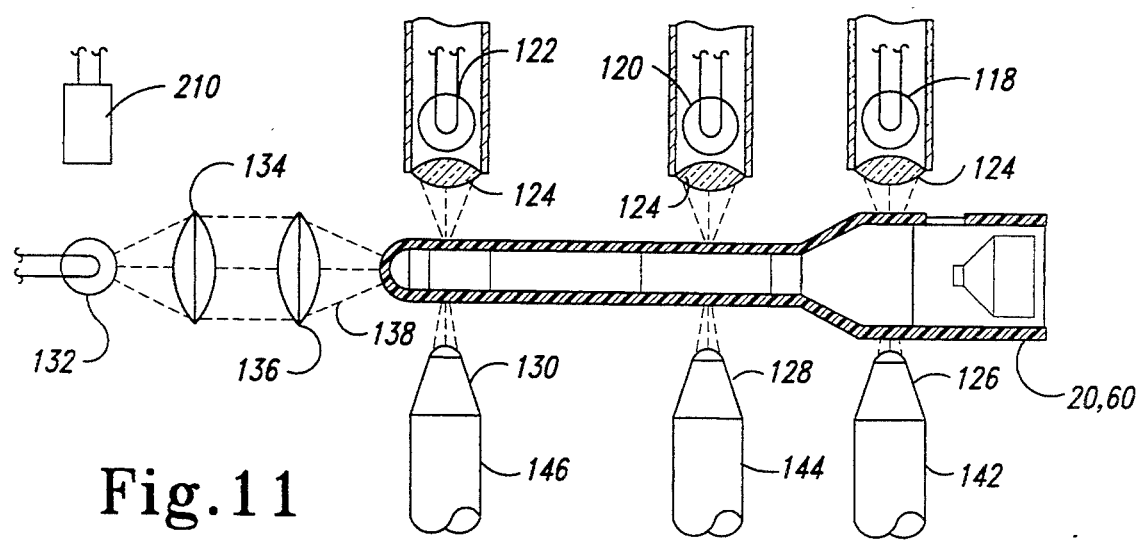
FIG. 11 is a schematic representation of a partial optical system illustrating the transverse and axial light sources and fiber optic detectors.
Figure 12:
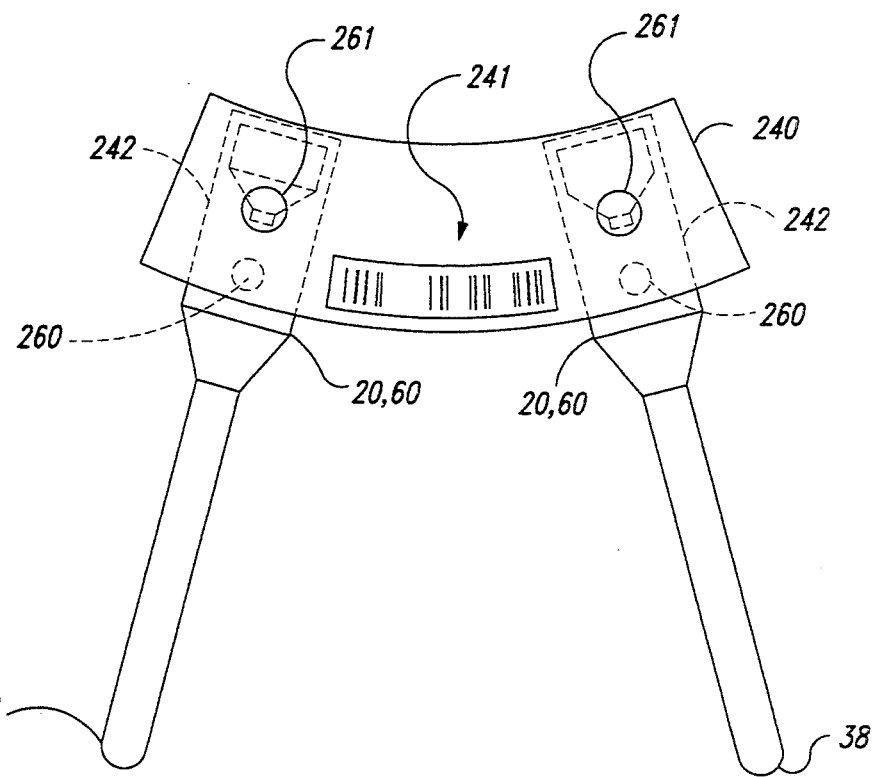
FIG. 12 is a top plan view of a bar code label for/use with the self-contained assay cartridges.

The instrument 70 employs a photometric system schematically represented in boxed in area 116 of FIG. 9 and mechanically illustrated in FIGS. 3, 8 and 11. The photometric system is capable of performing three transverse absorbance, calibration and other measurements at three positions along the axis of an assay cartridge 20, 60. The photometric system is also capable of axially illuminating the spherical end 38 of the cartridges for fluorescence, scattering and the like optical measurements.

Figure 2:
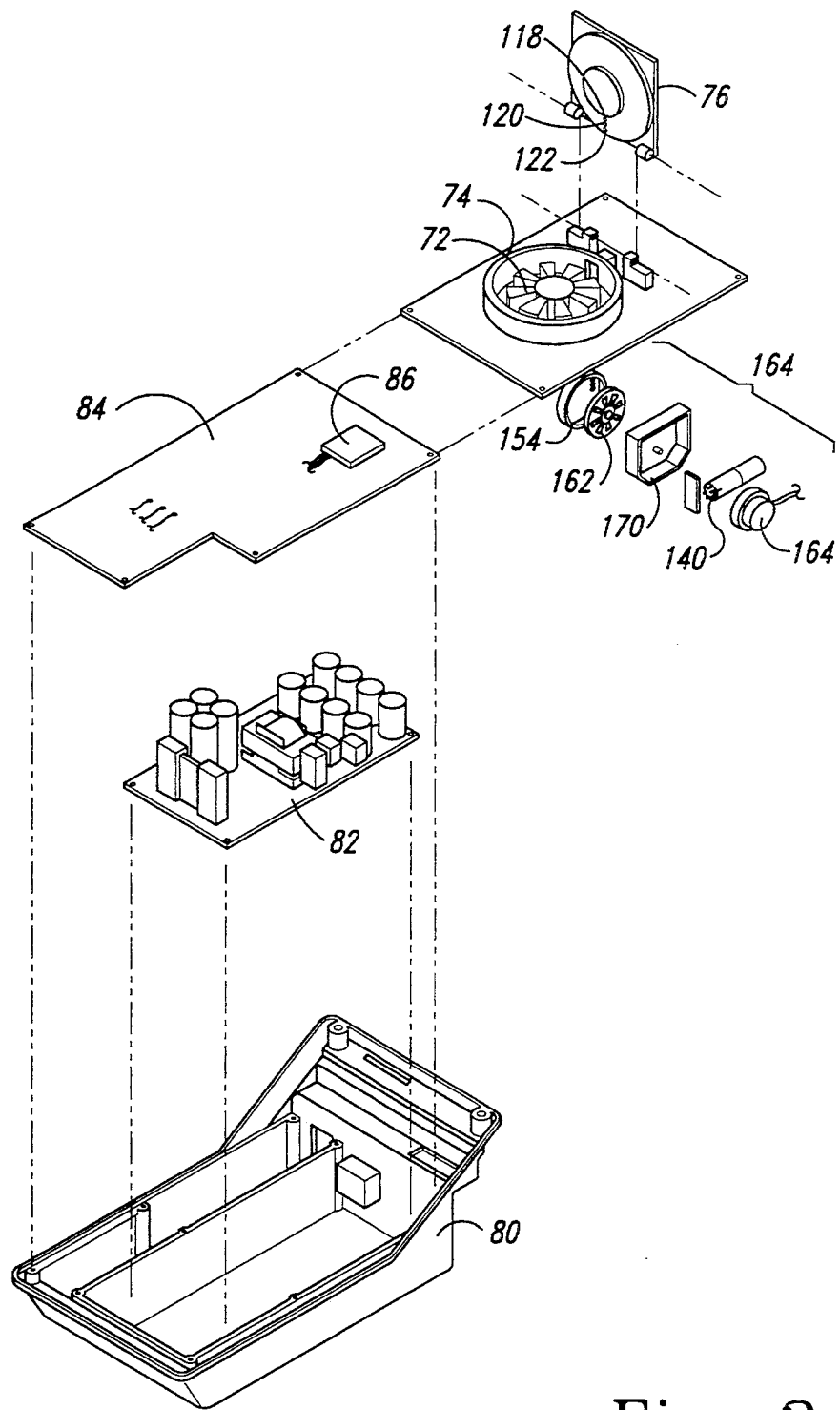
FIG. 2 is an "exploded" isometric view of the major components of the instrument shown in FIG. 1.

The photometric system shown in FIG. 11 includes first, second and third transverse light sources 118, 120 and 122, respectively. These sources are conventional 5 volt, 115 Ma incandescent lamps manufactured by Gilway Technical Lamp, Woburn, Mass., model 4115. Such lamps are preferred because of their ability to emit light over a wide bandwidth, including a portion of the ultraviolet spectrum and because they produce stable intensities shortly after start-up. For luminescence or fluorescence measurements the light sources may be turned off. As shown in FIG. 2, these lamps are housed in the pivotable lid 76. As shown in FIG. 11 these lamps are positioned so as to be spaced along one side of the cartridge 20, 60 axis when the cartridge is received in the cartridge carriage 72 and the lid 76 is closed. If only axial measurements are to be made, the transverse sources may be eliminated.

Each transverse light source is provided with a focusing lens 124. First, second and third fiber optic pick-ups 126, 128 and 130, respectively, protrude into the bowl 74 (see FIG. 8) so as to be positioned opposite the first second and third transverse light sources when cartridges are received in the carriage 74 and the lid 76 is closed. The cartridges have detection windows aligned with the light source/pick-up assemblies. This permits the instrument to perform absorbance measurements of reactions occurring in different axial layers of the cartridges. With the light source turned off luminescence measurements may be made.

An axially directed light source 132 is provided for the performance of fluorescence or light scattering determinations on the assay cartridges 20, 60. The third fiber optic pick-up 130 is conveniently used to detect fluorescent or scattered light emitted from the assay cartridge, without detecting direct illumination from the axially directed light source 132. When all light sources are turned off, luminescence from the cartridge is detected by fiber optic pick-up 130.

The axially directed light source is provided with a collimating lens 134 and a focusing lens 136 such that light beams 138 impinge upon the surface of the cartridge end 38 perpendicularly. A desirable geometry for the cartridge end is spherical. As is well known, a light ray which impinges upon a surface normal thereto is minimally reflected and refracted. Therefore, light emanating from the axially directed light source 132 is most efficiently transmitted through the spherical end 38 of the cartridge for stimulation of the fluorescent compounds in the cartridge. Fluorescent emission from the fluorescent compounds is collected at the third fiber optic pick-up 130. The bowl 74 is provided with a radial aperture 139 to admit the axially directed light beams 138. The fiber optic pick-ups 126, 128, 130 are connected to first, second and third fiber optic cables 142, 144, and 146, respectively.

As will be described further below, transverse absorbance and/or axial fluorescence measurements can be made for a variety of assays which may require wavelength filtration before detection of the transmitted or fluorescent, etc. light. The instrument 70 is advantageously provided with a detector assembly 92 (see FIGS. 2 and 3–6) which utilizes a single photomultiplier tube 140 to provide uniformity and comparability of measurements. One unique feature of the detector assembly is the ability to select from as many as four fiber optic light channels using up to four different detection modes with only one moving part.

As shown in FIGS. 3 and 5, the first, second and third fiber optic cables are connected to the detector assembly 92 by optical connectors 148, 150 and 152, respectively. The detector assembly 92 has a circular cover 154 defining first, second and third apertures 156, 158 and 160, respectively. These apertures correspond to the first, second and third transverse light sources respectively, while the third aperture also corresponds to the axially directed light source 132. Thus, three optical channels are provided for transferring light from a cartridge received in the carriage 72 to the single photomultiplier tube 140.

The circular cover 154 also houses a rotatable combination shutter/filter disk 162 which both selects one of the three channels for light transmission and filters the light in that channel appropriately. The disk 162 is connected for rotation to a stepper motor 164, which is controlled by the microprocessor 86. The front side of the disk shown in FIG. 6B has eight apertures 166 having an arc length separation S' which is greater than the arc length S subtended by two adjacent apertures (i.e., 156, 158) in the circular cover 154. That is, when one of the apertures 162 is aligned with one of the apertures 166, the remaining two apertures in the circular cover are obscured by the surface of the disk 162. Thus, only the light from one of the optical channels is transferred through the disk 162. Rotation of the disk simultaneously selects the appropriate channel and the appropriate wavelength for analysis.

As shown in FIG. 6A, the back side of the rotatable shutter/filter disk 162 is provided with eight different filters 168 which register with the apertures 166 in the disk. Thus, by selecting the appropriate one of the eight apertures 166 to open one of the three optical channels, the appropriate filter is also positioned at the selected channel. A frame 170 supports the detector assembly 92 within the instrument 70.

Referring to FIG. 9, the voltage gain of the photomultiplier tube 140 is selected by the microprocessor 86. The microprocessor controls a digital-to-analog converter 180 which drives a conventional high voltage supply 182 for the photomultiplier tube. The signals generated by the photomultiplier tube are preamplified in a conventional preamplifier 184, transferred to a conventional peak detection circuit 186 (not to be confused with a peak detection method for multiple measurements to be described below) and digitized by a fast analog-to-digital converter 188. A suitably fast analog-to-digital converter is model ADC 1005 manufactured by Natural Semiconductor, Inc., of Santa Cruz, Calif. The results of the fast analog-to-digital converter are delivered to the microprocessor for further processing as will be described below.

In addition to the above, an output display subassembly as indicated by boxed section 200 in FIG. 9 is provided. The output display subassembly includes the display 90 shown in FIGS. 1 and 7, a thermal printer 89, best seen in FIG. 7 with associated, conventional printer driver circuitry 204 under control of the microprocessor 86. One or more conventional RS232 interfaces 206 and associated multi-pinconnector 208 can be provided for connecting the instrument to a personal computer.

Photometric Analysis Method

As stated above, according to the assay cartridge selected and the specific assay procedure to be followed, photometric determinations of the cartridges can occur while the cartridges are loaded in the cartridge carriage which is rotating at speeds ranging from 1,000 to 10,000 rpm. This capability for high speed photometric determinations allows the instrument 70 to perform different assays in different cartridges in the same run, even where the assays require high speed centrifugation and photometric detection.

Figure 13:
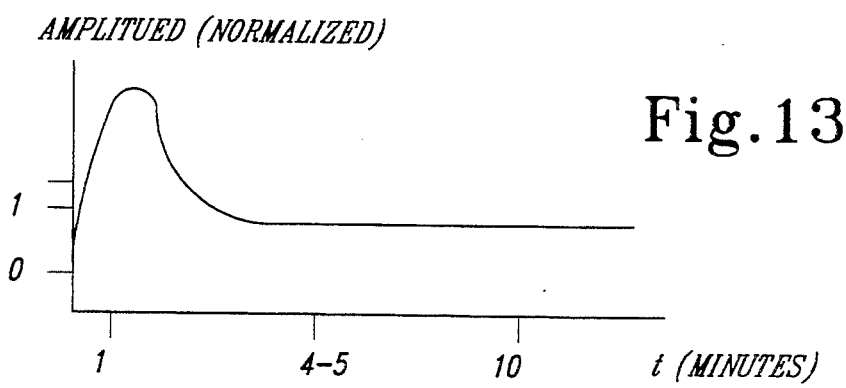
FIG. 13 is a graphic representation of the time varying amplitude characteristic of the axial light source shown in FIG. 11.

Furthermore, in order to ensure that accurate measurements are made, and to prevent the user from having to wait for a warm-up period, special photometric analysis techniques are used. Conventional automated photometric analysis instruments which require warm-up times of 30 to 40 minutes. However, the instrument 70 of the present invention is immediately usable even when "cold." A particular problem with incandescent light sources 118, 120, 122 and especially source 132 is that these sources tend to have an initial time-varying amplitude. In particular, source 132 does not reach a steady state value until after four to five minutes as shown in FIG. 13.

The associated memory of the microprocessor 86 is programmed with a correction factor algorithm which normalizes the value of each measurement with a preceding reference measurement. The correction algorithm is applied after photometric measurements have been taken.

For transverse light source 118–122, the reference intensity is determined as the photomultiplier 140 measures the light intensity as the rotor orifice located between cartridges 20, 60 is passing over the fiber optic pick-up. This occurs during slow speed rotation of the carriage 72 on start-up and also during higher speed rotation between cartridge measurements. The axially directed light source 132 has its own dedicated reference detector 210 for measuring the absolute magnitude thereof. Alternately the photomultiplier may be optically coupled to the axial light source for use as a reference detector instead of the dedicated reference detector 210. Furthermore, both the reference detector 210 and a second, complementary reference detector can be used together by optically coupling the axial light source directly to the photomultiplier through a fourth fiber optic cable and through a fourth position in the rotatable shutter/filter disk 162. With the above described method, photometric analysis of the assay cartridges can begin immediately after the instrument 70 is turned on without having to wait for completion of a long "warm-up" period.

Figure 14:
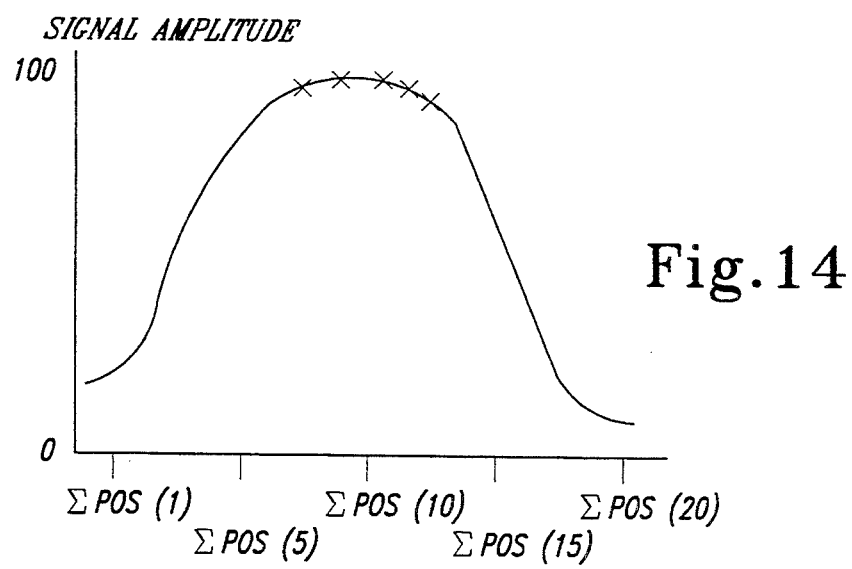
FIG. 14 is a graphic representation of signal amplitude through an assay cartridge at various positions with respect to the cartridge diameter.
Figure 15:
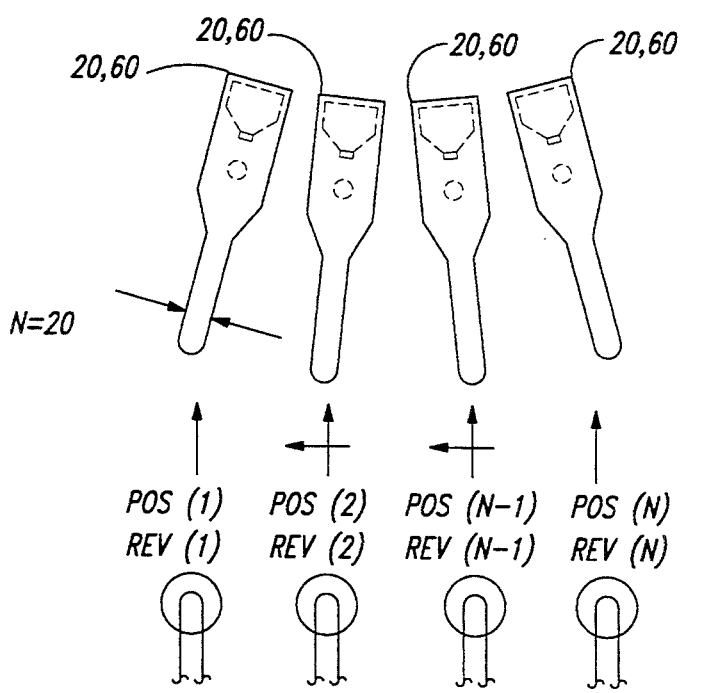
FIG. 15 is a schematic representation of a measurement technique which results in the signal amplitude distribution shown in FIG. 14.

In order to perform accurate photometric measurements of cartridges 20, 60 while rotating at speeds of up to 10,000 rpm, a specific measurement method, illustrated in FIGS. 14 and 15, is used. In this method, the microprocessor 86 divides each cartridge into radial slices (typically 20 to 40) within a "measurement window" which passes by the fixed detectors. This "measurement window" has a "width" of approximately 10% to 25% of the width of the area of optical interest. The "measurement window" is defined before performing a photometric measurement. This is possible because emitter/detector pairs 101 and 102 monitor the position of the rotating carriage 72 with respect to the light sources and fiber optic pick-ups. Sufficient position resolution is thus available to divide the cartridges (i.e. the measurement window) into at least 20 discrete radial segments.

As shown in FIG. 15, the microprocessor 86 begins measuring light intensity near or at the beginning of the defined "measurement window." During rotation in a first measurement revolution of the carriage, a first slice of the "measurement window" of the cartridge is illuminated by a light source and the reading is stored by the microprocessor. In the subsequent revolution, the second slice of the "measurement window" is illuminated and a second measurement is stored. This sequence continues until a 20th measurement is taken at a 20th slice of the "measurement window" as shown on the right side of FIG. 15. Thus, 20 measurements at different positions are taken for each cartridge in the carriage, typically within 20 revolutions. This operation is typically repeated four times so that the following measurements are taken:

Pos(n)'; Pos(n)"; Pos(n)'''; and Pos(n)'''' where n=1-20.

In the case of a fluorescence type measurement where the light emitted from the cartridge is directly proportional to the number of fluorescent molecules excited by the source, the four readings for each slice of the measurement window are summed, i.e., Pos(n)'+Pos(n)"+Pos(n)'''+Pos(n)''''=Sum(n), where n=1-20. A representative graph of the amplitudes of these summed readings at each measurement window position are shown in FIG. 14. As expected, small amplitudes are apparent at the first and last positions corresponding to the edges of the measurement window and maximum values are observed corresponding to positions in the middle of the measurement window (if a nonlinear measurement, such as an absorbance measurement were taken, each of the four measurements at a single position would be averaged rather than summed as is described further below). Summing or averaging of the measured values reduces the effects of small statistical variations (i.e., noise), thereby increasing the accuracy of the measurements.

In the example shown in FIG. 14, the five peak slices "X" would be summed to produce a single fluorescence measurement.

For colorimetric (absorbance) measurements, the photometric single is inversely proportional to color intensity in the cartridge. The absorbance signal is inverted to produce a profile of colorimetric signal intensity versus time similar to that shown in FIG. 14. Best precision and sensitivity is obtained by averaging several of the largest summed measurements (typically 5) at the middle of the colorimetric signal peak.

Only the actual measurements described above (not the computations) are performed while the carriage is rotating. The measurements are transferred directly to the microprocessor through the first analog-to-digital converter 188 during rotation. The above-described data manipulations are then performed by the microprocessor after the measurements have been collected. At the beginning of an assay, a data matrix is established by the microprocessor, according to the specific assay to be performed to store the expected measurements. For example, in some assays the data from the first optical channel (that of light source 118 in FIG. 11) will be analyzed with data from the second optical channel (that of light source 120 in FIG. 11).

A collar 240 having a machine readable label 241 can be provided to identify to the microprocessor 86 the assay which is to be performed. The collar has arms 242 which snap fit over or attach to one or more cartridges 20, 60. One of the cartridges may be an assay calibration control cartridge. The collar 240 positions the cartridges in a spaced-apart, fan-like relationship so that when the cartridge pair is loaded into the cartridge carriage 72, the cartridge axes are perpendicular to the rotation axis of the carriage with the spherical end 38 of the cartridges pointing away from the rotation axis. The collar includes optical apertures 260 for registration with the first optical channel. A patient sample aperture 261 registers with the thin wall membrane 36 (see FIGS. 10A and 10B) to permit introduction of patient sample into at least one of the cartridges with a syringe or the like.

As stated above, the collar 240 includes an optical bar code 241 which is read by conventional bar code sensor 280 in the lid 76 of the instrument 70 (see FIG. 7). On start-up, the microprocessor 86 directs the motor 94 to rotate the carriage 72 at a slow speed so that the information on the bar code 261 can be read by the bar code sensor 280. The bar code contains information relating to the chemicals contained in the cartridges and corresponds to a pre-recorded instruction set in the associated memory of the microprocessor for performing that particular assay. The microprocessor then operates the instrument to perform the correct sequence of spinning, heating, agitating and measuring for the particular assay.

Typical Operation

The instrument 70 described above can therefore automatically perform any variety of pre-programmed assays without the intervention of a skilled operator. The following is an example for one type of assay and is provided for illustration purposes only. In this example, an operator and the instrument 70 will perform the following steps.

1. The operator selects an appropriate pair of assay cartridges for performing a desired assay.
2. The operator adds patient sample into one of the cartridges (the other cartridge is an assay calibration control cartridge).
3. The selected cartridge pair is loaded into the instrument.
4. The operator pushes the start button 88.
5. The microprocessor 86 initiates a slow rotation of the cartridge carriage 72.
6. During slow rotation the emitter/detector pairs 101, 102 and the photometric system 116 determine the relative location of cartridges within the carriage.
7. The bar code sensor 280 reads the optically readable bar code 241. The code identifies the test type, lot number, expiration date, cartridge serial number, and assay calibration coefficients. The microprocessor then looks up the test sequence for the specific assay cartridge and sets up a data matrix for receiving data. The annular resistive heater 112 will be energized to maintain an incubation or other desired temperature. A brief high-speed spin may be initiated.

8. The microprocessor instructs the motor 94 to agitate the carriage while the cartridges are incubating or warming to operative temperatures.
9. Prior to the release of the reaction component 32, a high-speed spin may be necessary if the patient sample is whole blood rather than serum.
10. At the end of the incubation period if the assay is heterogeneous, the microprocessor instructs the motor to spin the carriage at high speed to transfer the solid phase with associated bound label through one or more immiscible layers.
11. During the high-speed spin, the microprocessor instructs the light sources to appropriately illuminate the cartridges. Measurements from the "measurement window" are stored in the data matrix.
12. Correction factors are applied to the measured data.
13. The multiple measurements are summed or averaged according to the optical interrogation method used. The corrected raw data is transferred by algorithms into appropriate units for each assay.
14. The results of the assay are displayed. The lid is automatically, partially opened to release hot air from inside the bowl 74.
15. The lid is completely opened when rotation is stopped.
16. The operator properly disposes of the used cartridges.

Other variations and embodiments of the invention are contemplated. Those skilled in the art will readily appreciate such variations upon carefully reviewing the above disclosure. Therefore, the invention is not to be limited by the above description, but is to be determined in scope by the claims which follow.

I claim:

1. A method for reading an assay cartridge having a known width with an interrogating light beam in an automated patient sample analysis instrument having a rotating carriage for receiving and centrifuging a plurality of self-contained, elongated assay cartridges, comprising the following steps:
    a) identifying and determining the position of each cartridge and defining a measurement window for each cartridge;
    b) dividing the width of each measurement window into (n) number of equally spaced measurement intervals;
    c) rotating the carriage at least (n) times;
    d) on each successive rotation, identifying a subject measurement interval and illuminating the cartridges with light from a light source and measuring the intensity of light emanating from the subject measurement interval of each cartridge so that after the carriage is rotated (n) times, (n) number of measurements, one for each of said (n) measurement intervals are taken for each cartridge;
    e) recording each of the (n) measurements for each cartridge;
    f) repeating steps c), d) and e) (x) number of times;
    g) averaging the (x) number of repeated measurements for each measurement interval and for each cartridge and recording the averaged resultant measurements; and
    h) selecting a number (y) of the largest averaged resultant measurements for each cartridge as indicative of a maximum measurement for each cartridge, whereby a reliable reading of absorption values of rapidly rotating cartridges is obtained.

2. The method of claim 1, wherein n=20, x=4, and y=5.

3. The method of claim 1, wherein the cartridges are positioned in the carriage in a spaced apart fashion with the cartridge axes perpendicular to a rotation axis of the carriage, wherein the cartridges are illuminated by a light source positioned so as to direct the interrogating light beam transverse to the cartridge axes when received in the carriage and wherein the light source has an initial time varying amplitude and a known steady state amplitude after warm up, including the steps of:
    measuring the intensity of light emitted from the light source when the light beam is between cartridges; and
    compensating for the amplitude variation before performing step g).

4. A method for reading an assay cartridge having a known width with an interrogating light beam in an automated patient sample analysis instrument having a rotating carriage for receiving and centrifuging a plurality of self-contained, elongated assay cartridges, wherein each cartridge has a plurality of axially positioned immiscible chemical layers for performing a predetermined assay, comprising the following steps:
    a) uniquely identifying and determining the position of each cartridge and defining a measurement window for each cartridge;
    b) dividing the width of each measurement window into (n) number of equally spaced measurement intervals;
    c) rotating the carriage at least (n) times;
    d) on each successive rotation, identifying a subject measurement interval and illuminating the cartridges with light from a light source and measuring the intensity of light emanating from the subject measurement interval of each cartridge so that after the carriage is rotated (n) times, (n) number of measurements, one for each of said (n) measurement intervals, are taken for each cartridge;
    e) recording each of the (n) measurements for each cartridge;
    f) repeating steps c), d) and e) (x) number of times;
    g) summing the (x) number of repeated measurements for each measurement interval and for each cartridge and recording the summed resultant measurements; and
    h) selecting a number (y) of the largest averaged resultant measurements for each cartridge as indicative of a maximum measurement for each cartridge, whereby a reliable reading of the assay cartridge with the interrogating light beam is obtained.

5. The method of claim 4, wherein n=20, x=4, and y=5.

6. A method for automatically performing analysis of patient sample with self-contained, elongated assay cartridges, wherein each cartridge has a preprinted assay code thereon and defines a cartridge axis and a reaction fluid contained in an internal receptacle sealed with a releasable seal, comprising the steps of:

providing an automated patient sample analysis instrument having a rotatable carriage for receiving and centrifuging a plurality of the assay cartridges in a spaced apart fashion, light emitters and a light detector for performing transverse absorption and axial fluorescence measurements, an optical reader for reading a preprinted assay code on the cartridges, a heater for controlling the temperature of the cartridges, and a controller having a memory for controlling the instrument, for storing measurements and predetermined assay procedures, and for performing calculations;

introducing patient sample into at least one cartridge and placing the cartridge into the carriage;

rotating the carriage at a first speed;

identifying the position of the cartridge in the carriage and reading the assay code thereon;

loading a matching assay procedure from the memory to the controller;

rotating the carriage at a second speed higher than the first speed to centrifuge the cartridge;

opening the releasable seal to cause the reaction fluid to be mixed with the patient sample;

reducing the carriage to a speed slower than the second speed;

incubating and agitating the cartridges;

increasing rotation of the carriage speed to the second speed;

reading measurements from the cartridges according to the predetermined assay procedures by a) dividing the width of each cartridge into (n) number of equally spaced measurement intervals;

b) rotating the carriage;

c) on each successive rotation, illuminating the cartridges with light from a light source and measuring the intensity of light emanating from each cartridge so that after the carriage has been rotated (n) times, (n) number of measurements, one for each of said (n) measurement intervals, are taken for each cartridge;

d) recording each of the (n) measurements for each cartridge;

e) repeating steps b), c) and d) (x) number of times;

f) averaging or summing the (x) number of repeated measurements for each measurement interval and for each cartridge and recording the averaged or summed resultant measurements; and g) selecting a number (y) of the largest averaged or summed resultant measurements for each cartridge as indicative of a maximum measurement for each cartridge, whereby a reliable reading of optical properties of rotating cartridges is obtained.

7. The method of claim 6, wherein $n=20$, $x=4$, and $y=5$.

* * * * *

UNITED STATES PATENT AND TRADEMARK OFFICE
CERTIFICATE OF CORRECTION

PATENT NO. : 5,449,621
DATED : September 12, 1995
INVENTOR(S) : Gerald L. Klein

It is certified that error appears in the above-indentified patent and that said Letters Patent is hereby corrected as shown below:

column 13, claim 6, lines 17 and 18, please delete "carnage" and insert therefor --carriage--.

Signed and Sealed this

Ninth Day of January, 1996

*Attest:*

BRUCE LEHMAN

*Attesting Officer*  *Commissioner of Patents and Trademarks*